(12) United States Patent
Nokes et al.

(10) Patent No.: US 9,376,697 B2
(45) Date of Patent: Jun. 28, 2016

(54) ON-FARM INTEGRATED HIGH-SOLIDS PROCESSING SYSTEM FOR BIOMASS

(71) Applicant: The University of Kentucky Research Foundation, Lexington, KY (US)

(72) Inventors: Sue E. Nokes, Lexington, KY (US); Bert C. Lynn, Nicholasville, KY (US); Stephen Rankin, Lexington, KY (US); Barbara Knutson, Lexington, KY (US); Michael D. Montross, Lexington, KY (US); Michael Flythe, Lexington, KY (US)

(73) Assignee: The University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 14/063,616

(22) Filed: Oct. 25, 2013

(65) Prior Publication Data

US 2014/0329285 A1 Nov. 6, 2014

Related U.S. Application Data

(60) Provisional application No. 61/818,130, filed on May 1, 2013.

(51) Int. Cl.
| | |
|---|---|
| *C12P 7/08* | (2006.01) |
| *C12P 7/10* | (2006.01) |
| *C12P 7/06* | (2006.01) |
| *C12P 19/02* | (2006.01) |
| *C12P 7/16* | (2006.01) |
| *C12P 7/28* | (2006.01) |
| *C12P 7/52* | (2006.01) |
| *C12P 7/54* | (2006.01) |
| *C12P 19/14* | (2006.01) |
| *C12P 21/00* | (2006.01) |
| *C12P 39/00* | (2006.01) |
| *C12N 9/42* | (2006.01) |

(52) U.S. Cl.
CPC .............. *C12P 19/02* (2013.01); *C12N 9/2437* (2013.01); *C12P 7/10* (2013.01); *C12P 7/16* (2013.01); *C12P 7/28* (2013.01); *C12P 7/52* (2013.01); *C12P 7/54* (2013.01); *C12P 19/14* (2013.01); *C12P 21/00* (2013.01); *C12P 39/00* (2013.01); *C12P 2201/00* (2013.01); *C12P 2203/00* (2013.01); *Y02E 50/10* (2013.01); *Y02E 50/16* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 4,891,320 A | 1/1990 | Aust et al. | |
| 4,965,086 A | 10/1990 | Helmling et al. | |
| 5,508,183 A | 4/1996 | Scott et al. | |
| 5,597,730 A | 1/1997 | Aust et al. | |
| 6,409,841 B1 | 6/2002 | Lombard | |
| 7,276,152 B2 | 10/2007 | Lin et al. | |
| 8,017,818 B2 | 9/2011 | Cortright et al. | |
| 2008/0057555 A1 | 3/2008 | Nguyen | |
| 2010/0120128 A1 | 5/2010 | Liang | |
| 2010/0159569 A1* | 6/2010 | Medoff | C08H 8/00 435/277 |
| 2010/0200806 A1 | 8/2010 | Medoff et al. | |
| 2011/0020884 A1* | 1/2011 | Latouf | C12P 7/10 435/136 |
| 2011/0183390 A1* | 7/2011 | Hickey | C12M 21/12 435/140 |
| 2011/0250638 A1 | 10/2011 | Sjoede et al. | |
| 2011/0308240 A1 | 12/2011 | Haghighi et al. | |

OTHER PUBLICATIONS

Demain et al., Microbiology and Molecular Biology Reviews, vol. 69, No. 1, pp. 124-154 (2005).*
Dictionary definition of "percolate," accessed on Nov. 4, 2015 at http://www.thefreedictionary.com/percolate.*
Demain et al., Microbiology and Molecular Biology Reviews, vol. 69, No. 1, pp. 124-154 (2005); of record.*

* cited by examiner

*Primary Examiner* — Soren Harward
*Assistant Examiner* — Paul D. Pyla
(74) *Attorney, Agent, or Firm* — King & Schickli, PLLC

(57) ABSTRACT

A method for on-farm processing a biomass feedstock into a useful industrial chemicals includes the steps of (a) delignifying the biomass feedstock to produce a delignified biomass, (b) subjecting the delignified biomass to cellulase production, (c) subjecting the delignified biomass with attached cellulase to simultaneous cellulolytic and solventogenic reactions to produce useful industrial chemicals (d) collecting and separating the useful industrial chemical from the fermentation broth and (e) collecting the fermentation residues.

16 Claims, 3 Drawing Sheets

ON-FARM INTEGRATED HIGH-SOLIDS PROCESSING SYSTEM FOR BIOMASS

This utility patent application claims the benefit of priority in U.S. Provisional Patent Application Ser. No. 61/818,130 filed on May 1, 2013, the entirety of the disclosure of which is incorporated herein by reference.

TECHNICAL FIELD

This document relates generally to consolidated high-solids on-farm biomass processing to produce useful industrial chemicals.

BACKGROUND

It is well known in the art to utilize various chemical and biological processes to convert biomass into useful industrial chemicals such as acetone, acetic acid, lactic acid, ethanol and n-butanol. Examples of such processes are disclosed in, for example, U.S. Patent Application Publication No. 2010/0159569 to Medoff et al., U.S. Patent Application Publication No. 2011/0308240 to Haghighi et al. and U.S. Pat. No. 6,409,841 to Lumbard.

This document relates specifically to consolidated on-farm biomass processing to produce industrial chemicals utilizing (a) existing on-farm storage technology, such as bunkers and vertical silos for industrial chemical production, (b) in situ delignification, followed by (c) cellulase production, (d) simultaneous cellulolytic and solventogenic reactions and (e) online product removal. Advantageously, the process disclosed in this document integrates well into the existing agricultural paradigm and brings greater profitability to the farmers that grow the biomass material. Advantageously, the process also produces useful petrochemical replacements and creates jobs in rural areas.

SUMMARY

In accordance with the purposes and benefits described herein a method is provided for processing a biomass feedstock into useful industrial chemicals. The method may be broadly described as comprising the steps of (a) delignifying the biomass feedstock to produce a delignified biomass; (b) subjecting the delignified biomass to cellulase production; (c) subjecting the delignified biomass with attached cellulase to simultaneous cellulolytic and solventogenic reactions to produce a fermentation broth including useful industrial chemicals and fermentation residues; (d) collecting and separating the useful industrial chemicals from the fermentation broth; and (e) removing fermentation residues and returning them to the farm. In one possible embodiment the method also includes repeating any or all of steps (a)-(d) before performing step (e).

In one useful embodiment the method includes using a biomimetic or biological reaction to delignify the biomass feedstock. That biomimetic reaction may be selected from a group consisting of Fenton chemistry, adding iron and peroxide to the biomass feedstock, adding a transition metal and peroxide to the biomass feedstock and combinations thereof. The biological reaction may be selected from a group consisting of adding fungus to the biomass feedstock, adding white-rot basidiomycete to the biomass feedstock and combinations thereof. The delignifying of the biomass feedstock may be performed by using a fungus selected from a member of the genus *Phanerochaete*.

In one possible embodiment the cellulase is produced by contacting the biomass feedstock with an anaerobic microorganism. In one embodiment that anaerobic microorganism is a thermophile. In another embodiment the anaerobic microorganism is a mesophile. In one possible embodiment the anaerobic microorganism for cellulase production is selected from the genus *Clostridium*. In another possible embodiment the anaerobic microorganism is selected from a genus *Thermobifida*. In yet another possible embodiment the anaerobic microorganism is selected from the genus *Fibrobacter*. In yet another possible embodiment the anaerobic microorganism for cellulolytic reaction is selected from the genus *Ruminococcus*. In yet another possible embodiment the anaerobic microorganism for cellulase production is selected from the genus *Butyrivibrio*. In yet another possible embodiment the anaerobic microorganisms for cellulase production are selected from a combination of any of these five genuses.

In one possible embodiment the simultaneous cellulolytic and solventogenic reaction is produced by contacting the biomass feedstock in the presence of cellulase with microorganisms selected from a genus group consisting of *Clostridium, Saccharomyces* and combinations thereof. In one possible embodiment, the method includes percolating water or media through the biomass feedstock as it is undergoing cellulolytic and solventogenic reactions. This is done to remove fermentation products and maintain favorable growth conditions for the reaction.

In some embodiments the method includes holding the biomass feedstock in a reaction vessel, maintaining a first set of reaction conditions in the reaction vessel when subjecting the delignified biomass to the production of cellulases to perform the cellulolytic reaction and maintaining a second, different set of reaction conditions in the reaction vessel when the delignified biomass and the biomass containing cellulases are subjected to the cellulolytic and solventogenic reactions. In such an embodiment the first set of reaction conditions include an anaerobic environment with thermophilic temperature (50-65° C.) or mesophilic temperatures (25-40° C.) and pH appropriate for proliferation of the cellulase producing microorganism. The second set of reaction conditions include an anaerobic environment with mesophilic temperature (25-40° C.) and pH appropriate for the proliferation of the cellulolytic and solventogenic reaction producing microorganism, with media replacement at prescribed intervals. In one possible embodiment different anaerobic microorganisms are used to complete the cellulase production to perform the cellulolytic reaction and the solventogenic reaction. By using different anaerobic microorganisms for each separate reaction, the effectiveness and efficiency of each reaction may be optimized for optimal processing results.

In accordance with additional aspects, an agricultural bulk storage system is utilized for the reaction vessel. More specifically describing the method, it further includes removing (a) lignin degradation products, (b) fermentation products (ie organic acids and ethanol) derived from the cellulase production for the subsequent hydrolysis of cellulose and (c) fermentation products (i.e. solvents and organic acids) derived from solventogenesis separately from the reaction vessel. In one possible embodiment the organic acids and solvents are then concentrated by counter current extraction with a hydrophobic, nontoxic solvent with limited solubility in water. Such a hydrophobic nontoxic solvent may be selected from a group consisting of mesitylene, kerosene, biodiesel gasoline, an alcohol heavier than hexanol, ester derivatives of fermentation products, oleyl alcohol, butyl butyrate, glycerol tributyrate and mixtures thereof. In another possible embodiment the solvents and organic acids are concentrated by adsorption using a hydrophobic high-surface area material selected from a group consisting of activated carbon, activated charcoal, high-silica hydrophobic zeolites, ion exchange resins, mesoporous silica-based adsorbents derived by silane chemistry and mixtures thereof.

In yet another possible embodiment the solvents and organic acids are concentrated by membrane separation using materials selected from a group consisting of a hydrophobic nonporous membrane through which the solvents pass selectively, a poly(dimethylsiloxane) membrane, a poly(tetrafluoroethylene) membrane, a poly(vinylidene fluoride) membrane, a porous membrane functionalized to promote pervaporation or perstraction of fementation-derived solvents, a poly(vinylidene fluoride) membrane, a poly(ethersulfone) membrane, an anodized alumina membrane, a track-etched polycarbonate membrane, a mesoporous silica-based membrane derived by surfactant templating and combinations thereof. Further, the method includes the step of returning fermentation residues to said farm by feeding to animals on the farm, gasifying at the farm, combusting at the farm or applying to land at the farm These and other embodiments of the method will be set forth in the description which follows, and in part will become apparent to those of ordinary skill in the art by reference to the following description and referenced drawing.

BRIEF DESCRIPTION OF THE DRAWINGS

The accompanying drawing incorporated herein and forming a part of the specification, illustrates several aspects of the current method and together with the description serve to explain certain principles thereof. In the drawings.

Reference will now be made in detail to the present preferred embodiments of the method, examples of which are illustrated in the accompanying drawing.

DETAILED DESCRIPTION

Figure 1:
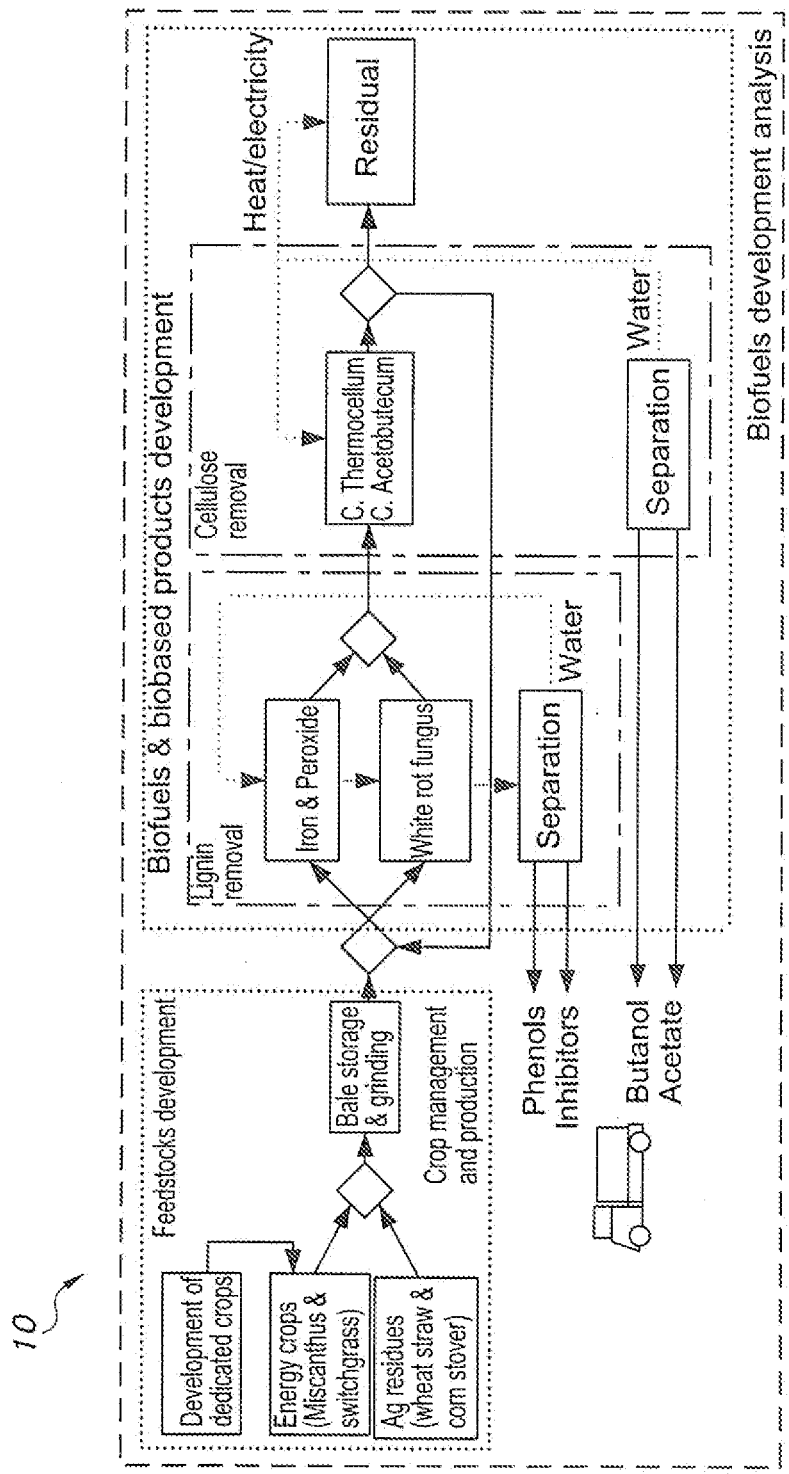
FIG. 1 is a schematical block diagram of the method.

A method of processing a biomass feedstock into useful industrial chemicals is generally illustrated in FIG. 1 by reference numeral 10. The biomass is harvested from a farm field. The biomass could be, for example, agricultural residues such as corn stover, or wheat straw or energy crops such as switchgrass and/or miscanthus that are baled or chopped. The bales could range from mid-size rectangular bales which may, for example, assume dimensions of approximately 1 m×1.3 m×2.6 m, to large rectangular bales, which may, for example assume dimensions of approximately 2.4 m×1.2× 0.9 m, or even large round bales (which may for example assume dimensions of approximately 1.8 m in diameter and 1.4 m wide). These bales are stored until time is available for processing. Chopped biomass could be used in the reaction vessel immediately or stored in an on-farm storage facility such as a vertical or horizontal silo, or an ag-bag.

At the time of processing, the bales are loaded into a reaction vessel which, advantageously, may take the form of an existing on-farm storage structure such as a horizontal bunker, a vertical silo, a round tank or the like. In one possible embodiment the biomass is provided in the reaction vessel at a specific packing density of approximately 11 lb/ft$^3$ to 21 lb/ft$^3$, and/or maintained in bales. In-situ delignification is then performed by chemical pretreatment or by inoculating the biomass feedstock with fungi or both in sequential applications with either treatment being applied first.

More specifically, the step of delignifying the biomass feedstock to produce a delignified biomass includes using a biological or biomimetic reaction. That biomimetic reaction may be selected from a group consisting of Fenton chemistry, adding iron and peroxide to the biomass feedstock, adding a transition metal and peroxide to the biomass feedstock and combinations thereof. The biological reaction may be performed using a fungus added to the biomass feedstock, for example adding white-rot basidiomycete to the biomass feedstock. In one possible embodiment the biomass is delignified by using a fungus selected from a member of a genus *Phanerochaete*. Useful members of that genus include, but are not necessarily limited to, *Phanerochaete aculeate, Phanerochaete affinis, Phanerochaete allantospora, Phanerochaete angustocystidiata, Phanerochaete argillacea, Phanerochaete arizonica, Phanerochaete australis, Phanerochaete avellanea, Phanerochaete brunnea, Phanerochaete brunneocystidiata, Phanerochaete burtii, Phanerochaete calotricha, Phanerochaete canolutea, Phanerochaete carnosa, Phanerochaete chrysorhiza, Phanerochaete chrysosporium, Phanerochaete deflectens, Phanerochaete ericina, Phanerochaete flava, Phanerochaete flavidoalba, Phanerochaete ginnsii, Phanerochaete hiulca, Phanerochaete intertexta, Phanerochaete laevis, Phanerochaete lamprocystidiata, Phanerochaete laxa, Phanerochaete leptoderma, Phanerochaete lutea, Phanerochaete magnolia, Phanerochaete odontoidea, Phanerochaete parmastoi, Phanerochaete pseudomagnoliae, Phanerochaete rimosa, Phanerochaete sanguinea, Phanerochaete sordida, Phanerochaete stereoides, Phanerochaete subceracea, Phanerochaete subglobosa, Phanerochaete subodontoidea, Phanerochaete taiwaniana, Phanerochaete tropica, Phanerochaete tuberculata, Phanerochaete velutina* and mixtures thereof.

Following delignification of the biomass feedstock, the delignified biomass is subjected to a reaction to produce cellulase. This cellulase is subsequently used to perform the cellulolytic reaction to hydrolyze cellulose in the biomass into carbohydrates, while coincidentally producing ethanol and organic acids. The cellulase production for the cellulolytic reaction is produced by contacting the biomass feedstock with an appropriate anaerobic microorganism. In one possible embodiment the anaerobic microorganism is a thermophile. In another possible embodiment the anaerobic microorganism is a mesophile. The anaerobic microorganism selected for cellulase production for the cellulolytic reaction may be from a genus group consisting of *Clostridium, Thermobifida, Fibrobacter, Ruminococcus, Butyrivibrio* and combinations thereof. More specifically, the anaerobic microorganism may be selected, for example, from a group consisting of *Clostridium thermocellum, Clostridium cellulolyticum, Clostridium cellulovorans, Clostridium lentocellum, Thermobifida fusca, Thermobifida cellulosilytica, Thermobifida alba, Fibrobacter succinogenes, Fibrobacter intestinalis, Ruminococcus albus, Ruminococcus flavefaciens, Ruminococcus champanellensis, Ruminococcus bromii, Ruminococcus gauvreauii, Ruminococcus lactaris, Butyrivibrio fibrisolvens, Butyrivibrio hungatei, Butyrivibrio crossotus, Butyrivibrio proteoclastic* and combinations thereof.

After completion of the production of cellulases for a certain interval of time, such as, for example, 48 hours, the delignified biomass with attached cellulases are subjected to simultaneous cellulolytic and solventogenic reactions to produce useful industrial chemicals and fermentation residues. The cellulolytic and solventogenic reaction is produced by contacting the biomass feedstock with active cellulases and microorganisms selected from a genus group consisting of *Clostridium, Saccharomyces* and combinations thereof. More specifically, the method includes using microorganisms selected from a group consisting of *Clostridium thermocellum, Clostridium acetobutylicum, Clostridium beijerinkii, Clostridium bifermentans, Clostridium kluyveri, Clostridium ljungdahii, Clostridium saccharolyticum, Clostridium saccharoperbutylacetonicum, Clostridium sporogenes, Saccharomyces boulardii, Saccharomyces arboricola, Saccharomyces bayanus, Saccharomyces cariocanus, Saccharomyces cariocus, Saccharomyces carlsbergensis, Saccharomyces castelli, Saccharomyces cerevisiae* and combinations thereof.

In order to maintain favorable anaerobic organism growth conditions for cellulolytic and solventogenic reaction, the method also includes percolating water or other appropriate media, such as RCM (reinforced clostridia medium), T-media (Thermophile media), or biological buffers such as $Na_2CO_3$ based buffer, and mixtures thereof, through the biomass feedstock as it is undergoing fermentation. This serves to remove the fermentation products which would otherwise become so concentrated as to limit or stop growth of the anaerobic microorganisms and thereby adversely affect the efficiency of the process.

In accordance with a significant aspect of the present method, the lignolytic reaction is completed in the same vessel as the simultaneous cellulolytic and the solventogenic reactions. In the present method the biomass is not physically processed, after harvesting prior to loading into the reactor. Since the biomass doesn't need to be cut and reduced in size, energy input has been reduced and loading the reactor has been simplified. The present method does not use a liquid fermentation system, where the biomass is suspended in liquid and remains in suspension by stirring. The present method uses a solid-substrate fermentation system, where the biomass remains fixed in place and water/media is percolated over the biomass. This approach also differs from prior art in that the biomass is not sterilized at any time during the process. Traditionally biomass is sterilized before or after pretreatment—another energy intensive process. Instead, chemical pretreatment, active temperature control, oxygen content, pH or a combination of the above are used to repress competing microorganisms. The lignolytic phase occurs at mesophilic conditions (25-40° C.), the cellulase-production phase occurs at either mesophilic (25-40° C.) or thermophilic (50-65° C.) temperatures, and the cellulolytic and solventogenic co-culture occurs at mesophilic (25-40° C.) temperatures. Further, in contrast to other methods, in this method cellulase is produced in the second step, but this enzyme complex hydrolyzes the biomass concurrently with solventogenesis. The solventogenic organisms uses the carbohydrates from the cellulase hydrolysis to produce industrial chemicals. In one possible embodiment, the environmental conditions in the solventogenesis phase are mesophilic, which is a sufficient temperature shift to slow the metabolism of the cellulolyltic organism, but allow its cellulase system to be active—producing carbohydrates but not much metabolic product (like organic acids and ethanol). This is done to ensure that the majority of the fermentation products come from the action of the solventogenic bacteria. Thus, the temperature is changed between *C. thermocellum* and the *C. beijerinckii* phases—*C. thermocellum*'s enzyme system will work at 35 C but *C. thermocellum* carbohydrate metabolism is markedly slowed at that temperature, leaving the released carbohydrates available for *C. beijerinckii* to use (but *C. beijerinckii* does not have an enzyme system and so cannot hydrolyze the biomass into carbohydrates).

Thus, it should be appreciated that the method includes holding biomass feedstock in a reaction vessel, maintaining a first set of reaction conditions in the reaction vessel when subjecting the delignified biomass to cellulase production for the subsequent cellulolytic reaction and maintaining a second, different set of reaction conditions in the reaction vessel when carbohydrates from the delignified biomass with attached cellulase (hydrolyzing the biomass) are subjected to the solventogenic reaction. In accordance with one embodiment the first set of reaction conditions include an anaerobic environment with thermophilic temperatures (50-65° C.) or mesophilic temperatures (25-40° C.) and pH appropriate for the health and proliferation of the anaerobic microorganism utilized for cellulase production. This phase may last for about 48 hours. Similarly a second set of reaction conditions favorable to solventogenic reaction include an anaerobic environment at mesophilic temperatures (25-40° C.) and pH appropriate for the health and proliferation of the microorganism, with continuous media replacement or media replacement at prescribe intervals of anywhere from five minutes to 48 hours. Significantly, by separating the cellulase production and solventogenic reactions into separate steps the best possible microorganisms for each reaction may be selected and the best possible conditions for those microorganisms may be provided to maximize the processing efficiency and produce the maximum amount of the desired industrial product in the shortest possible period of time.

All microorganisms utilized in the present method may be provided in inoculant bags of a type already used by dairy farmers to inoculate silage. Any heat needed for the elevated temperatures required for the operation of the reactor for the thermophilic and/or mesophilic microorganisms may be provided by burning waste material of the process if desired.

The method includes collecting and separating the useful industrial chemicals from the fermentation residues. Thus, it should be appreciated that the method includes removing (a) lignin degradation products, (b) organic acids and (c) solvents from the reaction vessel by percolating water or media through the reactor, flushing out the used media containing first lignin degradation products, and then subsequently organic acids and solvents. The flushed liquid will be processed to remove the organic acids and solvents in a concentrated stream, and the spent media/water will be recycled into the reactor. In one possible embodiment the method includes concentrating organic acids and solvents by counter current extraction with a hydrophobic, nontoxic solvent with limited solubility in water. Such a hydrophobic, nontoxic solvent may be selected from a group consisting of mesitylene, kerosene, biodiesel gasoline, an alcohol heavier than hexanol, ester derivatives of fermentation products, oleyl alcohol, butyl butyrate, glycerol tributyrate and mixtures thereof.

In another possible embodiment the method includes concentrating the organic acids and solvents by adsorption using a hydrophobic high-surface area material selected from a group consisting of activated carbon, activated charcoal, high-silica hydrophobic zeolites, ion exchange resins, mesoporous silica-based adsorbents derived by silane chemistry and mixtures thereof.

In yet another possible embodiment the method includes concentrating the organic acids and solvents by membrane separation using materials selected from a group consisting of a hydrophobic nonporous membranes through which the solvents pass selectively, a poly(dimethylsiloxane) membrane, a poly(tetrafluoroethylene) membrane, a poly(vinylidene fluoride) membrane, a porous membrane functionalized to promote pervaporation or perstraction of fementation-derived solvents, a poly(vinylidene fluoride) membrane, a poly(ethersulfone) membrane, an anodized alumina membrane, a track-etched polycarbonate membrane, a mesoporous silica-based membrane derived by surfactant templating and combinations thereof.

Still further the method also includes returning the fermentation residues to the farm. This may be done in a number of ways including, for example, by feeding to animals on the farm, gasifying at the farm, combusting at the farm or applying to land at the farm as a nutrient fertilizer. In accordance with yet another aspect, in one possible embodiment, the method includes repeating the delignifying, cellulase production and simultaneous cellulolytic and solventogenic reacting steps before performing the step of collecting the fermentation residues. Typically, the delignifying step or phase is completed within about five days, the cellulase production reaction is completed within about two days and the simultaneous cellulolytic and solventogenic phase is completed within about two days. The processes may be repeated one, two, three, four, five or even more times. Flushing is completed during the solventogenic phase anywhere from continuously to every 48 hours. Desired industrial chemicals are separated and collected and media and/or water may be returned to the reactor by an overhead spray system or other appropriate means. In one possible embodiment flushing is only completed during the solventogenic phase. However, media is reintroduced before each step. For example, the white rot grows in a different environment than the solvent producing bacteria. Thus, after the final solvent flush, the white rot is introduced into the reaction vessel with the white rot inoculum and media which replaced the bacterial media used in the solventogenic step. After the white rot has completed the majority of its delignifying, the thermocellum media is introduced. After the cellulase production phase, the C. beijerickii and inoculum is reintroduced such as through an overhead sprinkler system.

Advantageously, the sequential repeating of the (1) delignification, (2) cellulase production and (3) subsequent cellulolytic reaction and solventogenic reaction steps serves to progressively degrade the baled biomass from the outside into the center. By sequentially repeating this process the necessity of particle size reduction before treatment is eliminated, allowing the process to use baled biomass—saving energy and reactor loading time.

Figure 3:
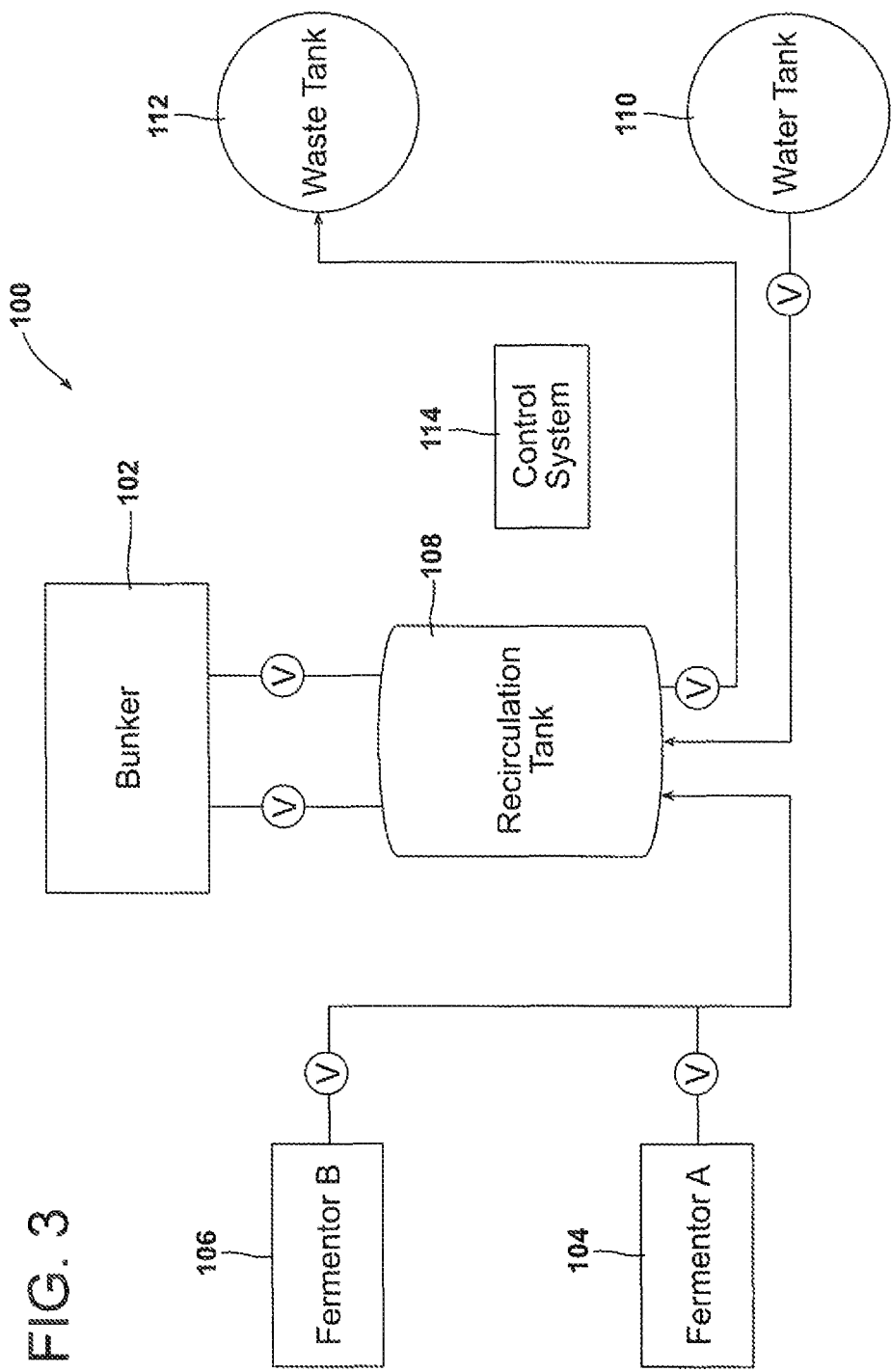
FIG. 3 is a schematic diagram of a pilot scale facility for completing the current method.

FIG. 3 illustrates a pilot scale facility 100 for completing the present method of on-farm processing of a biomass feedstock into useful industrial chemicals. That facility 100 includes a bunker or reactor 102 connected by various lines and control valves to a first fermenter 104, a second fermenter 106, a recirculation tank 108, a water tank 110 and a waste water tank 112. A control system 114 allows an operator to control the processing of the biomass feedstock at the facility 100.

In use, a bale of biomass feedstock is loaded into the bunker or reactor 102. Reactor 102 is equipped with a false floor which will allow liquid to drain beneath the bale and allow air to be introduced below the bale and circulated up through the bale. Reactor 102 will be sealed by placing the lid (reactor headplate) on the reactor and securing the headplate in place. The bale in reactor 102 will be wetted through overhead spray nozzles attached to the reactor headplate (not shown) with water from tank 110. Once the bale has achieved the desired water content, fungal inoculant from fermenter 104 will be introduced through the overhead delivery system in the reactor headplate. Reactor 102 will be aerated and maintained at a constant temperature using the control system 114, allowing fungal growth. The cellulolytic bacterium will begin growing in fermenter 106. Upon completion of the fungal pre-treatment, the reactor 102 will be inoculated with the cellulolytic bacteria produced in fermenter 106. Any drainage from the reactor upon inoculation will be collected and either sent to the waste tank 112 or sent to the holding tank for the separation process (not shown). The solventogenic bacteria will begin growing in fermenter 104 to be used in the next phase of the process. Reactor 102 will be held at anaerobic conditions, and the proper temperature and pH for this organism through the control system 114. Upon completion of the cellulase production portion of the cycle, the solventogenic bacterium will be introduced through the overhead delivery system. Any drainage from the reactor upon inoculation will be collected and either sent to the waste tank 112 or sent to the holding tank for the separation process (not shown). Reactor 102 will be held at anaerobic conditions, and the proper temperature and pH for this organism through the control system 114. Reactor 102 will be flushed with new water/media from the water tank 110 at regular intervals to remove the fermentation products. These products will be sent to the holding tank to be fed through the separation process to remove the fermentation products from the water/media. The water/media will be sent back to the recirculation tank 108 to be blended with the water/media from the water tank 110 during flushing/reinoculation. The system is designed such that any or all of these steps can be repeated as needed to achieve optimal conversion of the biomass in the bale.

The following example is presented to further illustrate the present method but it is not to be considered as limited thereto.

Example 1

Strains, Medium and Cultivation

The white-rot basidiomycete, *Phanerochaete chrysosoporium* (*P. chrysosoporium*) strain (ATCC MYA-4764) was obtained from the American Type Culture Collection (ATCC, Rockville, Md.) and maintained as a frozen culture (−80° C.) in 30% glycerol. Propagation of the organism for solid substrate cultivation was performed on Potato Dextrose Agar (PDA) plates for 5 days at 35° C.

*C. thermocellum* ATCC 27405 was obtained from ATCC and grown in basal medium that contained (per liter): 1530 mg $Na_2HPO_4$, 1500 mg $KH_2PO_4$, 500 mg $NH_4Cl_2$, 500 mg $(NH_4)_2SO_4$, 90 mg $MgCl_2.6H_2O$, 30 mg $CaCl_2$, 4000 mg yeast extract, 10 ml standard vitamins, 5 ml modified metals, 500 mg cysteine hydrochloride, 1 ml resazurin, and 4000 mg sodium carbonate. The medium pH was adjusted to 6.7 with NaOH and maintained under a 100% carbon dioxide atmosphere.

*C. beijerinckii* ATCC 824 was used in this study. For seed culture preparation, stock cultures were heat-shocked at 80° C. for 10 min, and transferred anaerobically into Reinforced *Clostridium* Medium (RCM) at 35° C. for 12 h.

On-Farm Processing System

The reactor system consists of a concrete bunker gravity drained with a wire mesh floor to hold the bales off the floor of the bunker, yet allow media to flow freely. The bunker is filled with large rectangular bales stacked in a uniform arrangement. The bales [corn stover (brought to 85% moisture content on wet basis)] were inoculated with *P. chrysosoporium* strain ATCC MYA-4764 with 2% (v/v) inoculum via an overhead spraying system. The reactor was maintained at 35° C. for 5 days. Our data show that up to 27% of the total lignin was removed after pretreatment.

After fungal pretreatment, the reactor with pretreated corn stover was inoculated with standard inoculum (see above)

yielding an initial inoculum of 0.176 g *C. thermocellum*/kg substrate. The reactor for the fermentation of *C. thermocellum* was held anaerobically at 65° C. for 2 days and then inoculated with *C. beijerinckii* at 0.5 g dry cell weight/kg substrate to initiate sequential co-culture at 35° C. for another 2 days. The aqueous solution was collected from the bottom of the reactor for analysis and product separation after the cycle of cellulolytic and solventogenesis phases ended. Then the fermentation reactor was flushed with T-medium and incubated at 65° C. for 2 days (no re-inoculation of *C. thermocellum* needed), followed by *C. beijerinckii* inoculation for acids and solvents production for 2 days. The entire flushing cycle has been repeated for 4 times and could be repeated for more cycles. $CO_2$ was flushed between each cycle to ensure anaerobic conditions.

The flushate from the cellulolytic/solventogenic phase of the fermentation is further processed to separate the fermentation products from the fermentation media. The fermentation media is recycled to the reactor, and the organic acids and solvents are stored as products. The fermentation products are separated from the media through a series of adsorption columns containing different adsorbents tailored to the products of interest.

Analytical Methods

Figure 2:
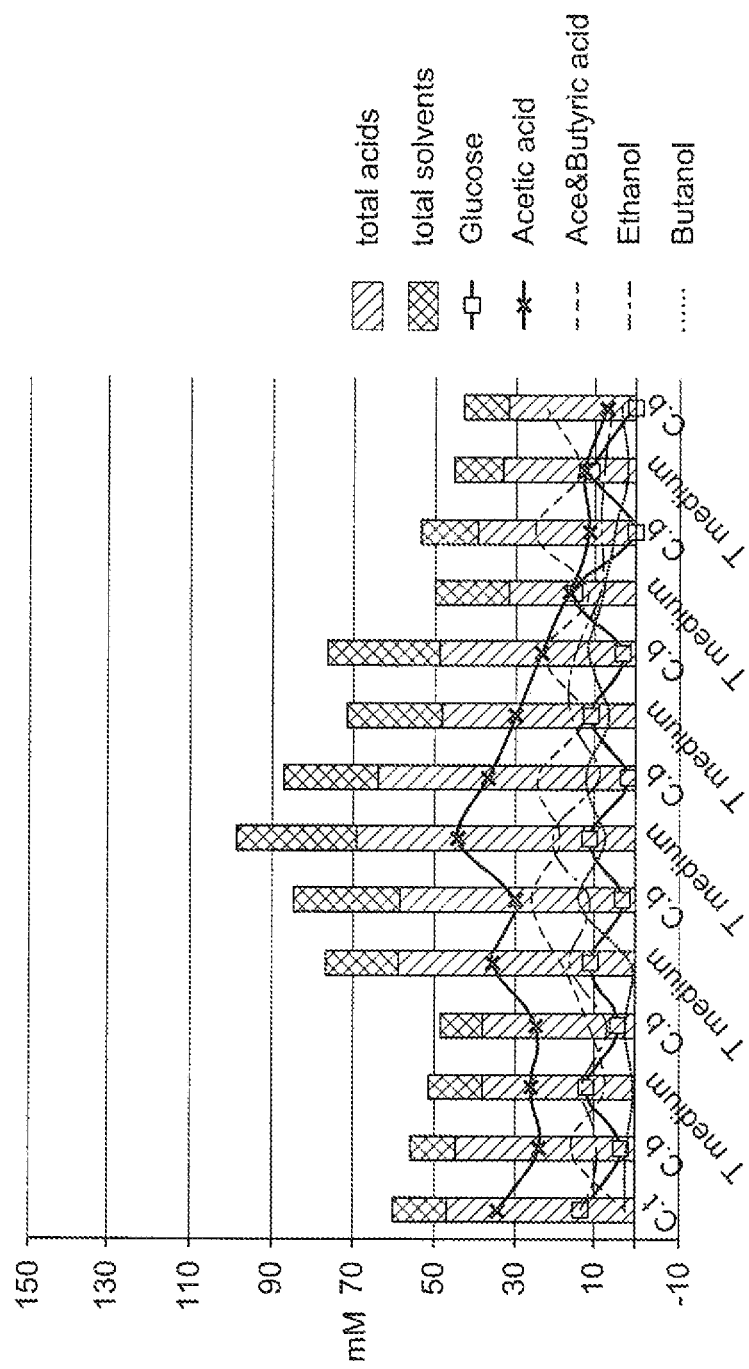
FIG. 2 is a plot showing production of glucose, acetic acid, acetone, butyric acid, ethanol and butanol from biomass using the present method.

Fermentation products (lactic acid, acetic acid, butyric acid, ethanol, butanol and acetone) were quantified by high-performance liquid chromatography (HPLC) using an Aminex HPX-87H column with a differential refractive index detector and an aqueous solution of 5 mM $H_2SO_4$ as the solvent. See FIG. 2.

The culture was re-incubated at 65 C and flushed with T medium. *C. thermocellum* could be maintained alive throughout sequential co culture at 35-37° C. and re incubation of *C. thermocellum* at 65° C. increased the availability of glucose by 2.8-4 fold.

TABLE 1

Products formed after four cycles of flush in various modes. The data comparison shows that re-inoculation of *C. thermocellum* did not actively improve the sequential co culture but would likely increase the operation cost.

| Flush process | Total product (mg/g CS) | | | | |
|---|---|---|---|---|---|
| | Acetic acid | Lactic acid | Butyric acid | Total acids | Total Butanol |
| Repeated flush and incubate at 65 C. | 60.13 | 11.56 | 71.002 | 142.72 | 18.73 |
| Repeated flush and Re-inoculation of C.t at 65 C. | 58.94 | 11.70 | 62.59 | 133.23 | 18.50 |

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

What is claimed:

1. A method of on-farm processing a biomass feedstock into useful industrial chemicals, comprising:
    (a) placing a non-sterilized biomass feedstock at a density of approximately 11 lb/ft³ to 21 lb/ft³ or maintained in bales on a false floor within a single sealed vessel with an overhead delivery system and delignifiying said biomass feedstock by adding a transition metal and a peroxide to produce a delignified biomass;
    (b) subjecting said delignified biomass from (a) to a solid-substrate reaction to produce cellulase, said solid-substrate reaction comprising inoculating the delignified biomass through the overhead delivery system with a thermophilic anaerobic microorganism and maintaining a first temperature range of 50-65° C. within the single sealed vessel to produce a delignified biomass with attached cellulase and to produce fermentation residues;
    (c) subjecting said delignified biomass with attached cellulase from (b) to a simultaneous cellulolytic and solventogenic solid-substrate reaction by inoculating the delignified biomass with attached cellulase of (b) with an anaerobic microorganism through the overhead delivery system and maintaining the single sealed vessel at a second temperature range of between 25-40° C. under anaerobic conditions to produce industrial chemicals and fermentation residues; and
    (d) percolating a media from the overhead delivery system through the biomass to remove fermentation residues and industrial chemicals during (b) and (c) and collecting said percolated media from beneath the false floor and separating industrial chemicals from said media and recycling the media back to the overhead delivery system.

2. The method of claim 1, including repeating any or all of steps (a)-(d), and then (e) collecting and using said fermentation residues on the farm.

3. The method of claim 2, wherein the transition metal is iron.

4. The method of claim 1, wherein said thermophilic anaerobic microorganism is a thermophile.

5. The method of claim 1, wherein the thermophilic anaerobic microorganism is selected from the group consisting of *Clostridium*, *Thermobifida*, *Fibrobacter*, *Ruminococcus*, *Butyrivibrio* and combinations thereof.

6. The method of claim 1, wherein the thermophilic anaerobic microorganism is selected from the group consisting of *Clostridium thermocellum*, *Clostridium cellulolyticum*, *Clostridium cellulovorans*, *Clostridium lentocellum*, *Thermobifida fusca*, *Thermobifida cellulosilytica*, *Thermobifida alba*, *Fibrobacter succinogenes*, *Fibrobacter intestinalis*, *Ruminococcus albus*, *Ruminococcus flavefaciens*, *Ruminococcus champanellensis*, *Ruminococcus bromii*, *Ruminococcus gauvreauii*, *Ruminococcus lactaris*, *Butyrivibrio fibrisolvens*, *Butyrivibrio hungatei*, *Butyrivibrio crossotus*, *Butyrivibrio proteoclastic* and combinations thereof.

7. The method of claim 1, wherein the anaerobic microorganism is selected from the group consisting of *Clostridium*, *Saccharomyces* and combinations thereof.

8. The method of claim 7, wherein the anaerobic microorganism is selected from the group consisting of *Clostridium thermocellum*, *Clostridium acetobutylicum*, *Clostridium beijerinkii*, *Clostridium bifermentans*, *Clostridium kluyveri*, *Clostridium ljungdahii*, *Clostridium saccharolyticum*, *Clostridium saccharoperbutylacetonicum*, *Clostridium sporogenes*, *Saccharomyces boulardii*, *Saccharomyces arboricola*, *Saccharomyces bayanus*, *Saccharomyces cariocanus*, *Saccharomyces cariocus*, *Saccharomyces carlsbergensis*, *Saccharomyces castelli*, *Saccharomyces cerevisiae* and combinations thereof.

9. The method of claim 8 including percolating water or media through said biomass feedstock as it is undergoing hydrolysis/solventogenesis so as to remove organic acids and solvents and maintain favorable anaerobic organism growth conditions for solventogenic reaction.

10. The method of claim 8, including holding said biomass feedstock in said vessel, maintaining a first set of reaction conditions in said vessel when subjecting said delignified biomass to cellulase production reaction and maintaining a second, different set of reaction conditions in said vessel when said delignified biomass with attached cellulase are subjected to simultaneous cellulolytic and solventogenic reactions.

11. The method of claim 10 including establishing said first and second set of reaction conditions by controlling an environmental condition, wherein the environmental condition is selected from the group consisting of chemical pretreatment, active temperature control, oxygen content, pH and a combination thereof to repress competing microorganisms.

12. The method of claim 10, wherein first set of reaction conditions include an anaerobic environment with thermophilic temperatures of between 50° C. and 65° C. and pH appropriate to the cellulase producing microorganism, and said second set of reaction conditions include an anaerobic environment with mesophilic temperatures of between 25° C. and 40° C. and pH appropriate to the solventogenic microorganism.

13. The method of claim 12, wherein said vessel in which said reactions occur is an agricultural bulk storage system.

14. The method of claim 13, further including removing (a) lignin degradation products, (b) fermentation products derived from cellulase production and (c) fermentation products derived from solventogenesis from said vessel.

15. The method of claim 14 including removing said fermentation products by membrane separation, wherein the membrane comprises a material selected from the group consisting of a hydrophobic nonporous membrane into which solvents dissolve selectively, a poly(dimethylsiloxane) membrane, a poly(tetrafluoroethylene) membrane, a poly(vinylidene fluoride) membrane, a porous membrane functionalized to promote pervaporation or perstraction of fementation-derived solvents, a poly(vinylidene fluoride) membrane, a poly(ethersulfone) membrane, an anodized alumina membrane, a track-etched polycarbonate membrane, a mesoporous silica-based membrane derived by surfactant templating and combinations thereof.

16. The method of claim 13 including returning fermentation residues to said farm by feeding to animals on said farm, gasifying at said farm, combusting at said farm or applying to land at said farm.

* * * * *